US00PP34968P2

(12) United States Plant Patent
Provost

(10) Patent No.: US PP34,968 P2
(45) Date of Patent: Feb. 7, 2023

(54) **NEW GUINEA *IMPATIENS* PLANT NAMED 'KLENI21160'**

(50) Latin Name: *Impatiens hawkeri*
Varietal Denomination: KLENI21160

(71) Applicant: Klemm+Sohn GmbH & Co. KG, Stuttgart (DE)

(72) Inventor: Roxane I. C. Provost, Stuttgart (DE)

(73) Assignee: KLEMM+SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 17/870,436

(22) Filed: Jul. 21, 2022

(51) Int. Cl.
*A01H 5/02* (2018.01)
*A01H 6/16* (2018.01)

(52) U.S. Cl.
USPC ..... Plt./318.7
CPC ..... *A01H 6/165* (2018.05)

(58) Field of Classification Search
USPC ..... Plt./318.7
CPC ..... A01H 6/165
See application file for complete search history.

*Primary Examiner* — Anne Marie Grunberg
(74) *Attorney, Agent, or Firm* — Weatherly IP Solutions, LLC; Barbara Campbell

(57) ABSTRACT

A New Guinea *Impatiens* plant particularly distinguished by red flowers and a v-shaped and ascending habit, is disclosed.

1 Drawing Sheet

Genus and species: *Impatiens hawkeri*.
Variety denomination: 'KLENI21160'.

BACKGROUND OF THE NEW PLANT

The present invention comprises a new and distinct variety of New Guinea *Impatiens*, botanically known as *Impatiens hawkeri*, and hereinafter referred to by the variety name 'KLENI21160'. 'KLENI21160' originated from a controlled hand-pollination between May to August 2015 in Kenya between the proprietary female New Guinea *Impatiens* variety 'NI-2015-0192' (unpatented) and the proprietary male New Guinea *Impatiens* variety 'NI-2015-0247' (unpatented).

The seeds from the cross were sown and plants were grown in a greenhouse for evaluation, where an individual plant designated 'KLENI21160' was selected from the group in May 2016. 'KLENI21160' was first vegetatively propagated via apical vegetative cuttings. 'KLENI21160' was found to reproduce true to type in successive generations of asexual propagation via apical vegetative cuttings.

SUMMARY

The following are the most outstanding and distinguishing characteristics of this new variety when grown under normal horticultural practices in Stuttgart, Germany.

1. Red flowers; and
2. A v-shaped and ascending habit.

DESCRIPTION OF THE PHOTOGRAPH

This New Guinea *Impatiens* plant is illustrated by the accompanying photograph which shows the plant's overall plant habit including form, foliage, and flowers. The photograph is of a 11-week-old plant grown in a greenhouse in Stuttgart, Germany in May 2020. The colors shown are as true as can be reasonably obtained by conventional photographic procedures.

DESCRIPTION OF THE NEW VARIETY

The following detailed descriptions set forth the distinctive characteristics of 'KLENI21160'. The data which define these characteristics were collected from asexual reproductions carried out in Stuttgart, Germany. Data was collected on 20-week-old plants grown in a greenhouse in Stuttgart, Germany in April 2022. Color references are to The R.H.S. Colour Chart of The Royal Horticultural Society of London (R.H.S.), 5$^{th}$ edition (2007), unless otherwise noted.

Classification:
- *Family*.—Balsaminaceae.
- *Botanical*.—*Impatiens hawkeri*.
- *Common*.—New Guinea *Impatiens*.
- *Designation*.—'KLENI21160'.

Parentage:
- *Female parent*.—The proprietary female New Guinea *Impatiens* variety 'NI-2015-0192'.
- *Male parent*.—The proprietary male New Guinea *Impatiens* variety 'NI-2015-0247' (unpatented).

Growth:
- *Propagation type*.—Vegetative, unrooted cuttings.
- *Growth habit*.—V-shaped.
- *Form*.—Ascending.
- *Flowering season*.—Spring.
- *Height*.—8.5 cm.
- *Width*.—19.0 cm.
- *Time to produce a finished flowering plant*.—8 weeks.
- *Time to initiate roots*.—3 weeks.
- *Root description*.—Fibrous.
- *Rooting habit*.—Vertical and fibrous.
- *Root color*.—RHS 159C (Orange-White).

Lateral branches:
- *Quantity of stems per plant*.—10 main stems.
- *Branching habit*.—Ascending.
- *Length*.—6.0 cm.
- *Diameter*.—0.4 cm.
- *Internode length*.—1.5 cm.
- *Texture and appearance*.—Smooth and glossy.

*Color*.—Developing (young): RHS 183A (Greyed-Purple). Developed (mature): RHS 183A (Greyed-Purple).

Leaves:

*Arrangement*.—Whorled on top, opposite on branches.
*Length*.—8.5 cm.
*Width*.—4.0 cm.
*Shape*.—Lanceolate.
*Apex*.—Broad.
*Base*.—Attenuate.
*Margin*.—Serrulate.
*Texture and appearance*.—Upper surface: Smooth and leathery. Lower surface: Smooth and glossy.
*Venation pattern*.—Arcuate.
*Venation color*.—Upper surface: RHS N137B (Green). Lower surface: RHS 137B (Green).
*Color, developing leaves*.—Upper surface: RHS 143B (Green). Lower surface: RHS 139C (Green).
*Color, fully expanded leaves*.—Upper surface: RHS 139A (Green). Lower surface: RHS 138C (Green).
*Petiole*.—Length: 1.0 cm. Diameter: 0.3 cm. Texture and appearance (both upper and lower surfaces): Smooth and glossy. Color: Upper part: RHS 184A (Greyed-Purple). Lower part: RHS 183B (Greyed-Purple).

Flower:

*Flower type and habit*.—Zygomorphic, simple, pendant.
*Flower longevity*.—Flowers continuously.
*Fragrance*.—Absent.
*Natural flowering season*.—Spring.
*Diameter*.—7.0 cm.
*Depth*.—0.5 cm.

Flower buds:

*Shape*.—Ovoid when completely closed; drop shaped when partially open.
*Length*.—2.0 cm.
*Diameter*.—1.0 cm.
*Texture and appearance*.—Smooth and leathery.
*Color*.—RHS 178A (Greyed-Red) and RHS 42A (Red).

Petals:

*Quantity and arrangement*.—5.
*Length*.—Banner petal: 2.5 cm. Lateral petals: 3.0 cm. Lower petals: 3.0 cm.
*Width*.—Banner petal: 5.0 cm. Lateral petals: 4.0 cm. Lower petals: 4.0 cm.
*Shape, all petals*.—Cordate.
*Apex, all petals*.—Emarginate.
*Base, all petals*.—Round to acute.
*Margin all petals*.—Entire.
*Texture and appearance, all petals, both upper and lower surfaces*.—Smooth and satiny.
*Color, all petals, when opening*.—Upper surface: RHS 42A (Red). Lower surface: RHS 42C (Red).
*Color, all petals, fully opened*.—Upper surface: RHS 44A (Red). Lower surface: RHS 44C (Red).

Sepals:

*Quantity and arrangement*.—4 lateral and 1 spurred arrangement: whorled.
*Lateral sepal*.—Length: 1.5 cm. Width: 0.7 cm. Shape: Elliptic. Apex: Caudate. Base: Rounded. Margin: Entire. Texture and appearance: Upper surface: Puberulent and leathery. Lower surface: Smooth and glossy. Color: Upper surface: RHS N34A (Orange-Red). Lower surface: RHS 46C (Red).
*Spurred sepal*.—Length, not including spur: 1.2 cm. Width, proximally: 1.2 cm. Shape, proximally: Obtuse. Base: Rounded. Margin, proximally: Entire. Texture and appearance, proximally: Upper surface: Puberulent and leathery. Lower surface: Smooth and glossy. Color, proximally: Upper surface: RHS 47C (Red). Lower surface: HRS 47C (Red). Spur: Length: 6.0 cm. Diameter: 0.2 cm. Shape: Needle-shaped. Texture and appearance: Smooth and glossy. Color: RHS 185A (Greyed-Purple).

Peduncles:

*Length*.—6.0 cm.
*Diameter*.—0.2 cm.
*Angle*.—45 degrees ascending.
*Texture and appearance*.—Smooth.
*Strength*.—Moderately strong.
*Color*.—RHS 184A (Greyed-Purple).

Reproductive organs:

*Stamens*.—Quantity per flower: 5 stamens are fused and form a cap over the ovary. Filament length: Not visible. Filament color: Not visible. Anther length: 0.1 cm. Anther shape: Monothecal. Anther color: RHS 158C (Yellow-White). Pollen color: RHS 8D (Yellow). Pollen amount: Abundant.
*Pistils*.—Quantity per flower: 1. Pistil length: 0.6 cm. Stigma shape: Truncado. Stigma color: RHS 145B (Yellow-Green). Style length: 0.5 cm. Style color: RHS 143A (Green). Ovary color: RHS 145C (Yellow-Green).

Fruit and seed set: Seed set not observed to date.

Disease and pest/insect resistance: No disease and pest/insect resistance observed to date.

COMPARISON WITH PARENTAL LINES AND KNOWN VARIETY

'KLENI21160' can be distinguished from its parents as described in Table 1.

TABLE 1

Comparison with Parental Lines

| Characteristic | 'KLENI21160' | Female Parent 'NI-2015-0192' | Male Parent 'NI-2015-0247' |
|---|---|---|---|
| Flower color | A lighter, more-true red than 'NI-2015-0247' | Orange and white bi-color | Darker red than 'KLENI21160' |

'KLENI21160' is most similar to the commercial New Guinea *Impatiens* variety COLORPOWER 'Red' (unpatented). Differences between the varieties are described in Table 2.

TABLE 2

Comparison with Similar Variety

| Characteristic | 'KLENI21160' | COLORPOWER 'Red' |
|---|---|---|
| Flower size | Larger than COLORPOWER 'Red' | Smaller than 'KLENI21160' |

I claim:

1. A new and distinct variety of New Guinea *Impatiens* plant designated 'KLENI21160' as illustrated and described herein.

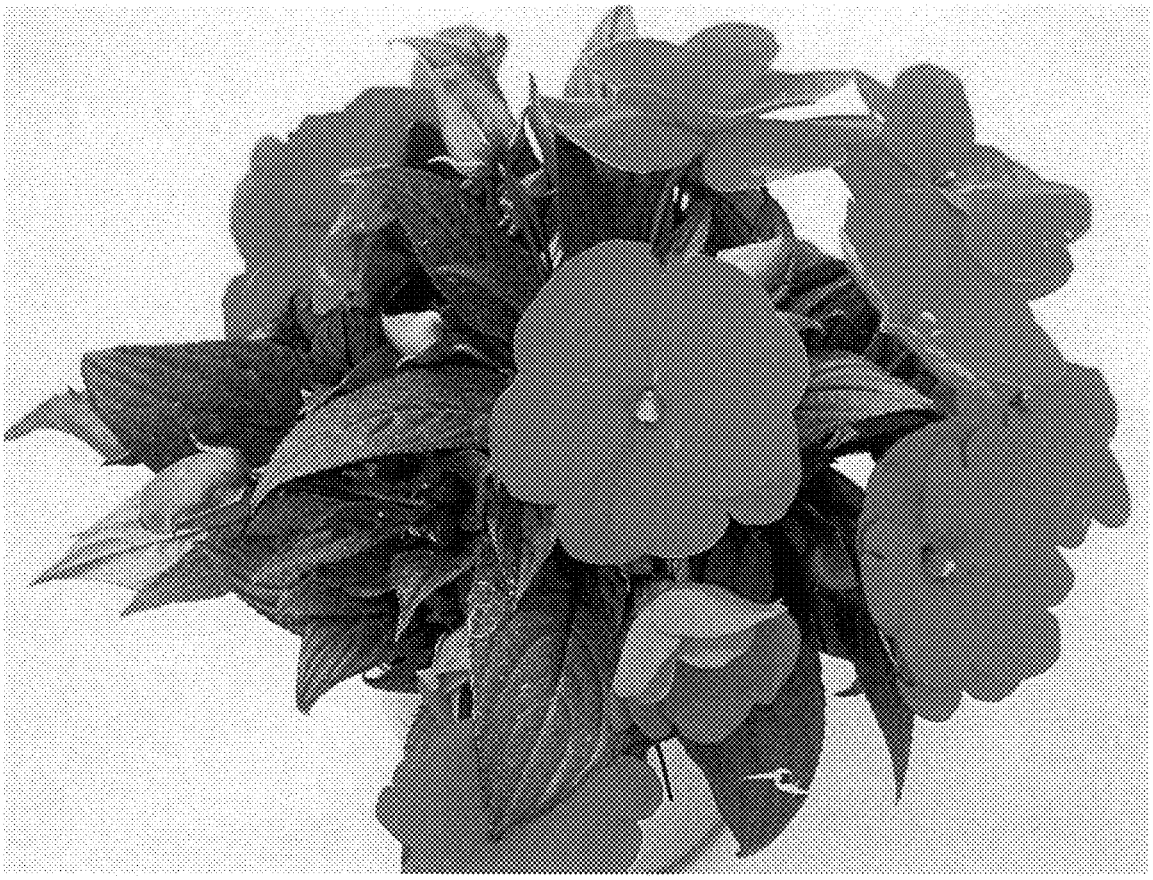

* * * * *